United States Patent

Campbell, Jr.

[11] Patent Number: 5,800,434
[45] Date of Patent: Sep. 1, 1998

[54] SEGMENTAL RIB CARRIAGE INSTRUMENTATION AND ASSOCIATED METHODS

[76] Inventor: Robert M. Campbell, Jr., 415 Stone Wood, San Antonio, Tex. 78216

[21] Appl. No.: 819,877

[22] Filed: Mar. 18, 1997

Related U.S. Application Data

[62] Division of Ser. No. 356,235, Jan. 16, 1995, Pat. No. 5,632,744.

[51] Int. Cl.⁶ ............................................. A61B 17/70
[52] U.S. Cl. ...................... 606/61; 606/60; 606/72; 606/74; 606/86
[58] Field of Search .................... 606/60, 61, 72, 606/74, 86, 53; 623/66

[56] References Cited

U.S. PATENT DOCUMENTS 5,261,908  11/1993  Campbell, Jr. ............... 606/61
5,514,132   5/1996  Csematony et al. ........... 606/60

*Primary Examiner*—Michael Buiz
*Assistant Examiner*—Daphna Shai
*Attorney, Agent, or Firm*—David G. Henry

[57] ABSTRACT

Applicant's invention includes an apparatus and associated method for treating or managing spinal deformities, including scoliosis, abnormal kyphosis, vertebral fractures and tumors, through attachment of spinal rods to ribs adjacent to the spine, rather than to the spine itself. The attachment member are designed whereby the ribs are completely encircled once the rods and attachment member are fully implanted, thereby virtually eliminating the chance of inadvertent dislodging of the rods.

6 Claims, 4 Drawing Sheets ns 5,800,434

SEGMENTAL RIB CARRIAGE INSTRUMENTATION AND ASSOCIATED METHODS

CITATION TO PRIOR U.S. APPLICATION(S)

This is a divisional of application Ser. No. 08/356,235 filed on Jan. 16, 1995 U.S. Pat. No. 5,632,744.

This is a divisional application with respect to a U.S. application filed by the present Applicant on Jun. 8, 1992 (Ser. No. 07/895,377) from which Priority is Claimed.

A PCT application (Ser. No. PCT/US93/05474), claiming Priority from U.S. Ser. No. 07/895,377, was filed on Jun. 8, 1993, and the resulting U.S. national stage application (U.S. Ser. No. 08/356,235) was filed on Jan. 16, 1995 now U.S. Pat. No. 5,632,744.

The classification of the present claims, is within Class 623, Subclass 66, according to Examiner R. Green in his restriction requirement of Jan. 7, 1993 in application U.S. Ser. No. 07/895,377.

Applicant claims priority from all of the above applications pursuant to applicable law. Inventorship with respect to all claims is in Applicant, Robert M. Campbell, Jr.

BACKGROUND OF THE INVENTION

1. Field of The Invention

Applicant's invention relates to diseases and symptoms evidenced as deformities in the human skeletal systems.

2. Background Information

The human spine is a system which consists of a succession of vertebral bodies which, in its normal state, extends within and defines a single sagittal plane. Ideally, there should be substantially no deviation in the frontal plane (perpendicular to the sagittal plane from a straight line. Within the sagittal plane, a certain degree of lumbar lordosis and thoracic kyphosis is normal and desirable. An excess degree of lumbar curvature is known as hyperlordosis, while an abnormally flat lumbar succession of vertebral bodies is known as hypolordosis. In like manner, hyperkyphosis (most commonly seen in Scheuermann's disease) is that condition evidenced by a greater-than-normal degree of curvature in the thoracic spine which gives a hump-back type appearance.

Scoliosis may be defined as lateral deviation and rotation of a series of vertebrae from the midline anatomic position of the normal spine axis. The deformity occurs in three planes—frontal, sagittal and transverse. Scoliosis, in its more severe embodiments, is a debilitating, if not deadly disease. With the progression of the curve, structural changes occur in the vertebrae and in the formation and contour of the rib cage. This, in turn, often threatens respiratory function and capacity. The curvature of the spine itself can pose danger to the spinal cord. Still further, the interrelationships between other thoracic and abdominal organs are changes and the normal function thereof is imperilled. Fully 80% of all scoliosis cases are idiopathic, i.e. the cause is cause unknown.

There is no present "cure" for scoliosis as such, but treatments of the symptoms have been known for some time—treatments with often-times questionable effectiveness, inherent intra-surgical danger to the patient, frequent patient discomfort and/or substantial inconvenience, and substantial likelihood of post-operative complication.

Non-surgical control of scoliosis (as distinguished from correction) is available. Such non-surgical treatments include physical therapy, biofeedback, electrical stimulation and orthosis (the Sayre cast, the Hibbs and Risser casts, the Milwaukee brace, the Boston brace and the Wilmington brace, for example). Reportedly, however, these non-surgical methods can collectively boast, at most, only a 70% success rate in arresting further progression of scoliosis in cases of proven curve progression in growing (relatively immature) spines. Many of these non-surgical methods are contraindicated in cases involving curvatures greater than a specific range (usually about 40 degrees), certain patients with physical infirmities in addition to the scoliosis, patients with certain remaining growth potential, and/or with patients who cannot be reasonably expected to rigorously follow a prescribed therapeutic regimen or to emotionally tolerate the limitations and appearances of the various braces.

Surgical intervention in the correction of scoliotic curvature presently involves spinal instrumentation and spinal fusion first pioneered by Hibbs, et al.[1] One without the other is generally viewed as ineffective under current convention. The over-all objective of the surgical intervention is to correct the scoliosis as much as is possible, and to restore compensation of the spine with a symmetrical trunk and with head, neck and shoulders centered over the pelvis; and to stabilize the spine and prevent curve progression. The objective of the spinal instrumentation portion of surgical treatment of scoliosis is to immediately correct curvature to the degree possible and to immobilize the spine in the corrected orientation until a solid fusion has taken place.

[1] Hibbs, R. A., Risser, J. C. and Ferguson, A. B.: "Scoliosis treated by the fusion operation." *J. Bone Joint Surg.*, 6:3, 1924.

Problems abound with currently available spinal instrumentation. Some instrumentation occupies space needed for the bone graft placed over the posterior spine. Also, the attachment means used for spinal instrumentation inherently risks intra-operative spinal cord damage with the potential for irreversible paralysis. Still further, many spinal instrumentation systems are prone to disengagement because their attachment schemes involve screws (prone to disengage from atrophic vertebrae) or hooks which only partially encircle vertebral body projections (prone to dislodging during movement).

"Harrington Instrumentation"[2,3] is the posterior spinal instrumentation by which all current systems are compared. Harrington instrumentation is "segmental instrumentation" which by definition involves the interlocking of vertebral components and fixation at multiple levels for imparting corrective forces. In this system, bone-purchasing hooks are attached to posterior elements of the spine—facets, laminae, and transverse processes. Through these hooks, distraction forces are applied to the concave side of the spinal curve by the ratchet principle, and compression forces are applied on the convex side of the thoracic curve at the base of the transverse processes and adjusted by the threadnut principle.

[2] Harrington, P. R.: Treatment of Scoliosis. Correction and internal fixation by spine instrumentation. *J. Bone Joint Surg.*, 44-A:591, 1962.
[3] Harrington, P. R.: Surgical instrumentation for management of scoliosis. *J. Bone Joint Surg.*, 42-A:1448, 196.

Despite its prominence, the Harrington system has drawbacks: (1) failure of derotation of the spine as the distraction force straightens the lateral curvature; as a result the rib hump is not corrected; (2) the distraction forces of the Harrington instrumentation flatten the spine with the result that the normal lumbar lordosis is obliterated thereby producing a marked deformity; (3) Harrington instrumentation does not provide enough stability to the spine and, therefore, postoperative immobilization is required in the form of a cast or spinal orthosis. In the use of the Harrington Rod to distract spinal curves in young growing children with scoliosis when posterior spinal fusion is contraindicated: (1) the bulky nature of the Harrington instrumentation is such that it protrudes well beyond the normal dorsal contour thereby "tenting up" the overlying skin and causing breakdown problems; and (2) Harrington instrumentation without fusion is prone to loosening and fracture when serially expanded to accommodate growth in cases of implantation in children; and (3) direct surgical exposure of the osseous posterior spinal components in association with any spinal instrumentation often promotes inadvertent spinal fusion.

Another modified Harrington instrumentation system is the Moe Rod, developed by Dr. John Moe for use in growing children with scoliosis requiring surgical spinal stabilization without posterior spinal fusion. The Moe Rod is identical to the Harrington Distraction Rod, except that it is threaded at both ends to engage distraction hooks for serial expansion. The complications associated with use of the Moe Rod are similar to those described above with reference to the original Harrington Rod approach.

A form of segmental instrumentation for treatment of scoliosis was developed by Dr. Eduardo Luque of Mexico. Luque's system involved positioning two contoured smooth "L" spinal rods on either side of the posterior spinous processes and wiring them directly to the underlying laminae through wires at each vertebral level of the scoliosis.

Luque's procedure involves passing multiple wires through the spinal canal to wrap around the laminae and carries with it a substantial risk of spinal cord damage. Additional detractions from the Luque system include an attendant excessive operative time with significant blood loss and the obscuring of areas where normally one would want to effect biologic fusion. This methodology has gained meaningful acceptance only in treating paralytic scoliosis.

A relatively new system of segmental instrumentation (the Cotrel-Dubousset [C-D] Instrumentation[4]) addresses many of the Harrington system's shortfalls and lacks some of the drawbacks of the Luque system. Nevertheless, C-D instrumentation exhibits its own shortcomings, the principle one being that it is complex and cumbersome, with too many "moving parts". Also, implantation is extremely complex and requires the skills and experience possessed by few practitioners. It obscures the posterior spine; limiting the amount of bone graft surface for biologic fusion.

[4] Cotrel, Y. and Dubousset, J.: New Segmental posterior instrumentation of the spine. *Orthop. Trans.*, 9:118, 1985.

CD instrumentation is a dual rod system which the affixation of rods to and on either side of the spine through attachment to posterior elements thereof. CD instrumentation is attached by way of pedicle hooks that slide under the lamina to engage the underlying pedicle with the U-shaped edge of a hook, or through laminae hooks which are cupped around the lamina or the transverse process and are directed either proximally or distally to provide either compressive or distractive forces as are needed to act as appropriate corrective forces.

CD instrumentation includes knurled spinal rods which are contoured to the general shape of the curved spine after various compression or distraction hooks are applied at frequent intervals along the spine. Usually, the distal and proximal hooks have a hole for the rod to be threaded through them and the intermediate hooks are opened posteriorly so that the rod can be slipped into the hook itself. Cylindrical sleeves, known as blockers, will have been threaded onto the shaft and then, once the rod is placed into a hook, the blocker is pushed into the hook to trap the rod inside the hook and a compression set screw locks the rod into the blocker. The blockers are unidirectional and must be positioned so as to be directed up and down into a hook to provide proper compression to the hook so it gains purchase on the bone.

The hooks are then loosened somewhat and the rod on the convex side of the scoliotic curve is then rotated medially. This tends to correct the curve as much as possible and converts the scoliosis to a more normal kyphosis. At this point, the second rod is inserted on the concave side and a similar maneuver is performed. Once the rotation is either completed and the spine is completely straight (or partial rotation is only possible because of rigidity of the curve) then the hooks are tightened somewhat. Additional correction can be obtained by using compression or distraction pliers to move the hooks along the spinal rod at this point to provide either compression or distraction along segmental parts of the curve.

Once final positioning is obtained, as much bone as possible is maneuvered through and around the bulky instrumentation to the posterior elements of the spine which previously will have been decorticated for promoting biological fusion of the posterior spine. The final step is to apply two transverse load devices which link the two rods into a three dimensional, integrated, stable structure for maintaining proper corrective forces and desired spinal orientation and alignment.

One current form of anterior segmental instrumentation for treatment of scoliosis is the Zielke instrumentation[5]. This system, however, obviously involves accessing the anterior surfaces of the spinal column to attach instrumentation. This, in turn, carries a significant risk of neural and vascular injury with the accompanying risk of partial or total paralysis.

[5] Zielke, K. and Pellin, B.: Neue Instrumente and Implantate zur Erganzung des Harrington Systems. *Z Orthop. Chirl*, 114: 534, 1976.

The history of scoliosis and its treatment yields as its lesson a seeming paradox: it is dangerous (and often ineffective) to treat the spine in addressing spine anomalies. This paradox has heretofore remained unsolved for two primary reasons: (1) the causation and mechanisms of scoliosis are not understood and, therefore, cannot be addressed in a preventative or even curative manner; and (2) direct management of an affected system (in this case the spine) is the traditional approach common to virtually all orthopedic procedures, a predisposition which yields a myopic view of the possible remedies as evidenced by the spinal instrumentation of the prior art.

SUMMARY OF THE INVENTION

It is an object of the present invention to provide novel and non-obvious instrumentation for treatment and management of scoliosis.

It is another object of the present invention to provide a novel method for the treatment and management of scoliosis.

It is another object of the present invention to provide instrumentation of the treatment and management of scoliosis which instrumentation avoids direct affixation to vertebrae.

It is another object of the present invention to provide a method for the treatment and management of scoliosis which method does not involve direct affixation of instrumentation to spinal components.

It is another object of the present invention to provide novel instrumentation for the treatment and management of scoliosis the implantation of which instrumentation involves less risk of injury to the recipient than does presently available instrumentation.

It is another object of the present invention to provide novel method for the treatment and management of scoliosis which method involves less risk of injury to the recipient of treatment therethrough than does presently available methods of treatment and management.

It is another object of the present invention to provide novel instrumentation for the treatment and management of scoliosis which instrumentation is less prone to produce deleterious, post-operative side effects than do presently available instrumentation systems.

It is another object of the present invention to provide novel instrumentation for the treatment and management of scoliosis which instrumentation, when implanted, lies lateral to the spinal column and does not, therefore, obstruct access to the vertebrae to be fused as part of scoliosis treatment.

It is another object of the present invention to provide novel instrumentation for the treatment and management of scoliosis the implantation of which instrumentation, because of simplified rib attachment means, lacks any substantial requirement of special training or prior experience over that possessed by most skilled orthopedic surgeons.

It is another object of the present invention to provide novel improvements to existing spinal instrumentation which is used in the treatment and management of scoliosis, such improvements relating to the attachment methodology involved in the implantation of such instrumentation which attachment methodology yields a substantially more secure implantation which is substantially less prone to inadvertent dislodging than instrumentation implanted through presently practice methodology and utilized instrumentation.

It is another object of the present invention to provide novel attachment means for use with presently available spinal instrumentation attachment means permits attachment of the instrumentation to ribs as opposed to the spine.

It is another object of the present invention to provide a method for utilizing presently available spinal instrumentation which is used in the treatment and management of scoliosis, which method carries less risk of spinal cord injury than presently practiced procedures associated with implantation of such instrumentation.

It is another object of the present invention to provide a method for utilizing presently available spinal instrumentation which is used in the treatment and management of scoliosis, which method involves attachment of such instrumentation to ribs rather than directly to the spine.

In satisfaction of these and related objectives, Applicant's present invention provides, instrumentation and associated methods of use thereof in the treatment and management of scoliosis through manipulation, not of the spine, but of the adjacent ribs.

Applicant's invention includes affixation components which are useable with certain components of presently available spinal instrumentation (spinal rods) as are used in the treatment and management of scoliosis. Such affixation components and associated methodology permit affixation of presently utilized spinal instrumentation to ribs, rather than directly to posterior spinal components. This affixation scheme carries substantially less risk of spinal cord injury than presently practiced methodology and additionally affords an enhanced mechanical advantage in achieving derotation of the spine as is desired in treatment of scoliosis—this latter benefit reflecting the greater moment of torque which is available by virtue of the spatial separation between the points of attachment of the instrumentation and the vertebral bodies to which corrective forces are desired to be applied.

The devices of Applicant's present invention also afford a substantially enhanced reliability factor as compared to presently known instrumentation in that they completely encircle the involved attachment ribs and, absent catastrophic injury, are virtually incapable of inadvertent disengagement.

By prescribing the attachment of instrumentation lateral to the spine rather than to the spine itself, Applicant's invention avoids the impediments to biological fusion attending the use of prior spinal instrumentation which overlies and substantially hinders access to the posterior elements of the spine.

Auxiliary components prescribed by Applicant's invention include arched cross member bridge for integrating the instrumentation lying on either side of the spine and thereby forming a system which operates in three dimensions in providing corrective forces to a scoliotic curve. The arch shape is necessary as an accommodation to the more laterally disposed attachment positions of Applicant's instrumentation as compared other spinal instrumentation which allow more planer cross members.

While the treatment of scoliosis is a primary application of Applicant's invention, the methodology and equipment prescribed herein are also applicable to the management of deformities arising from or at least threatened by vertebral fractures and tumors. By attaching spinal rods to ribs on either side of a vertebral fracture or tumor, one thereby stabilizes the spinal column adjacent to the defect whereby stresses are removed from the affected vertebral body(ies) to allow, as applicable, healing and/or resection.

Further still, Applicant's herein described instrumentation and methodology is adaptable for use in treating hyperkyphosis. By conforming the spinal rods to the desired degree of curvature, and attaching them to ribs adjacent the deformity, a correction can be achieved without direct involvement of the spine with the attendant hazards of such involvement as described above.

DETAILED DESCRIPTION OF THE PREFERRED EMBODIMENT

Figure 1:
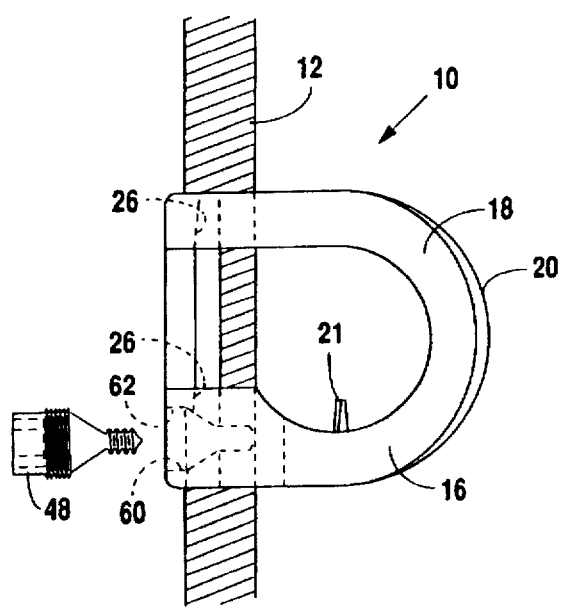
FIG. 1 is an elevational, partially exploded side view of a rib carriage of Applicant's invention shown installed on a spinal rod with the cam nut thereof exploded laterally.

Referring to FIG. 1, a rib carriage is identified generally by the reference numeral 10. Rib carriage 10 is shown installed on a spinal rod 12. Spinal rod 12 is a conventional rod such as is used according to Cotrel's methodology for treatment of scoliosis.

Figure 12:
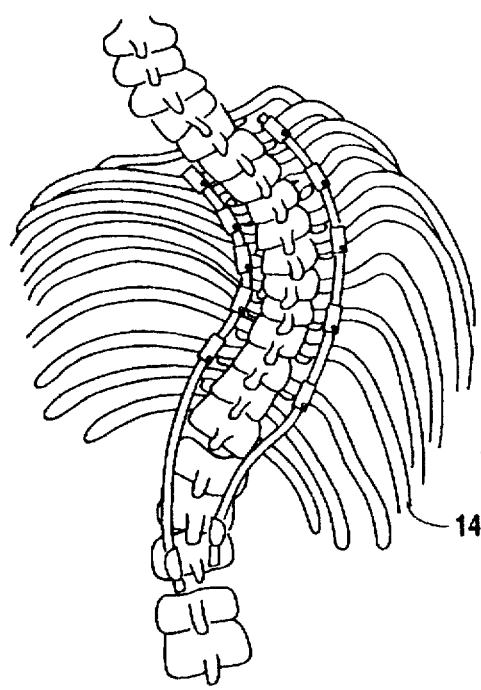
FIG. 12 is a posterior view representation of spinal rods implanted according to Applicant's invention prior to rotation of the rods to effect correction of the scoliotic curvature.

Referring principally to FIG. 12, as its name implies, rib carriages 10 attaches to a recipient's ribs 14. The attachment loci as prescribed by Applicant's methodology are directly adjacent to the transverse process/rib junction of each respective rib 14, medial to the anatomical posterior angle of the rib 14.

Referring again to FIG. 1, and also to FIGS. 2, 3, 4, 5, 6 and 7, rib carriage 10 includes a loop unit 16. The loop unit 16 comprises two partial loops 18 and 20 which are for partially encircling a recipient's ribs 14. Partial loops 18 and 20 each exhibit an optional stabilization peg 21 which is for positively engaging a rib 14 to prevent lateral shifting of the rib carriage 10 after implantation.

In any given case, the partial loops 18 and 20 of each rib carriage 10 should be sized such that they loosely encircle the intended recipient's ribs 14. The path of the partial loops 18 and 20 about the rib 14 is, as is evident from the drawings, circular. By contrast, ribs 14 would be better described as being oblong. Shaped this manner, the partial loops 18 and 20 "cradle" the ribs 14 at a point of minimum contact as opposed to deleteriously compressing the ribs 14.

The loose encirclement of the ribs 14 in the attachment of Applicant's rib carriages 10 is an important aspect of Applicant's invention for several independently significant reasons. The circular circumvention of the partial loops 18 and 20 permits the rib carriage 10 to slightly pivot relative to the ribs 14. This is important, in part, because the rib carriages 10 slightly change orientation relative to the ribs 14 to which they are attached as the spinal rods 12 are oriented for the desired corrective action.

The ability of the rib carriages 10 to pivot is further important in allowing the over-all spinal instrumentation to partially accommodate traumatic force which may occur in falls, etc. and thereby not transfer the total of the force to the natural ribs 14 in a manner which would likely fracture the ribs 14. If the rib carriages 10 were rigidly attached to ribs 14, the rib carriages 10 would apply a possibly damaging torque to the ribs 14 in response to a traumatic force to the spinal rod 12. This is substantially avoided by the circular path of circumvention suggested herein. Also, the relatively loose circumvention of the ribs 14 obviates the danger of rib ischemia at the site of contact between the partial loops 18 and 20 and the rib 14 surface. Still further, the gentle movement permitted by the preferred mode of attachment for the rib carriage 10 and brought about by normal movement of the recipient has the tendency to promote work hypertrophy in the rib 14 thereby actually strengthening the rib 14.

Figure 3:
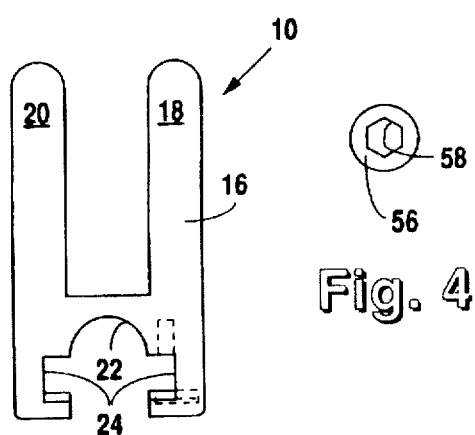
FIG. 3 is a top plan view of the rib carriage of Applicant's invention shown installed on a spinal rod.
Figure 4:
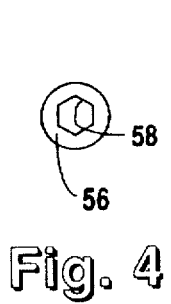
FIG. 4 is an elevational front view of the cam nut of Applicant's rib carriage.

Referring principally to FIG. 3 each terminus of each partial loop 18 and 20 is contoured to exhibit a semi-circular recess 22. The two recesses 22 of each partial loop 18 and 20 are shaped and oriented to respectively define segments of approximately one-half of a single cylindrical space which space substantially corresponds to the space occupied by the spinal rod 12 which extends between and beyond the two recesses 22. The recesses 22 of the preferred embodiment of Applicant's rib carriage 10 are defined by a slightly smaller radius of curvature than the annular surface of the spinal rods 12 with which they are to mate. Accordingly, the spinal rods 12 tend to lodge in the recesses 22 of their respective rib carriages 10 even before they are actually locked into place.

Referring principally to FIGS. 3, 5, 6 and 7, the termini of partial loops 18 and 20 are further contoured to exhibit recesses 24 lateral to each recess 22 to receive therethrough a portion of a cam insert 40. Cam insert 40, when installed as to be described hereafter, serves to securely lock the rib carriage 10 into place on a spinal rod 12.

Cam insert 40 exhibits a length-wise semi-circular recess 42 which, like recess 22 of the ring unit 16, defines a segment of approximately (slightly less than) one-half of a single cylindrical space which space substantially corresponds to a space occupied by a like axial length of the spinal rod 12. Cam insert 40 is a wedge-like component exhibiting two cam inclines 42 and 44 which are positioned along with length of the cam insert 40 to interact with complimentary cam inclines 26 and 28 of the ring unit 16 adjacent to each recess 22. As cam insert 40 is forced into its fully installed position relative to the ring unit 16 (with the spinal rod 12 in position as shown in FIG. 1), the interaction of cam inclines 42 and 44 of cam insert 40 with cam inclines 26 and 28 of the ring unit 16 serves to forcibly draw the ring unit 16 and the cam insert 40 together thereby securely clamping the spinal rod 12 therebetween.

Figure 2:
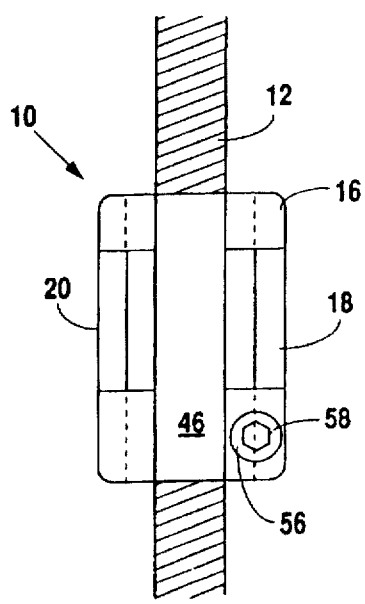
FIG. 2 is an elevational front view of the rib carriage of Applicant's invention shown installed on a spinal rod.
Figure 7:
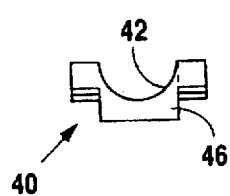
FIG. 7 is a top plan view of the cam insert of Applicant's rib carriage.
Figure 8:
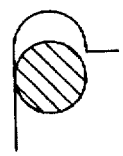
FIG. 8 is a partially cross-sectional, top plan view of the interaction between a spinal rod and a complimentary recess of the ring unit of Applicant's unit.

Referring principally to FIGS. 2 and 7, a ridge 46 extends lengthwise on cam insert 40 between the cam inclines and on the opposite side of cam insert 40 from recess 42. Ridge 46 is designed to define, in cooperation with the adjacent portions of ring unit 16, a substantially flat surface opposite the partial loops 18 and 20 when the rib carriage 10 is installed and locked into place with cam insert 40.

Figure 9:
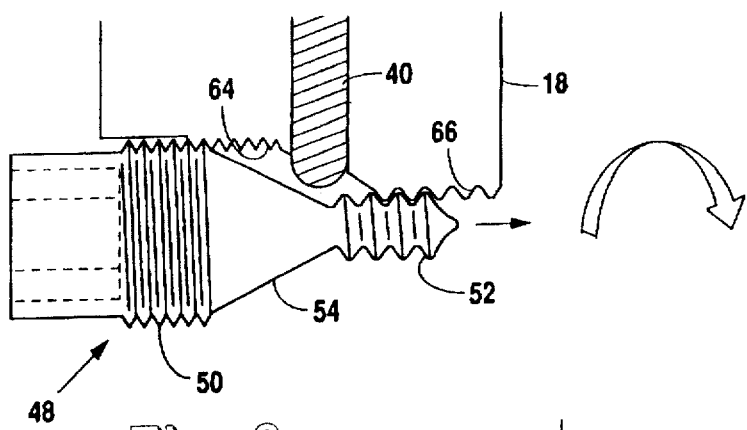
FIG. 9 is an elevational, partial cross sectional view of the interaction between the cam nut, the ring unit and the cam insert of Applicant's rib carriage at the initial stage of insertion of the cam nut into the recess of the ring unit.
Figure 10:
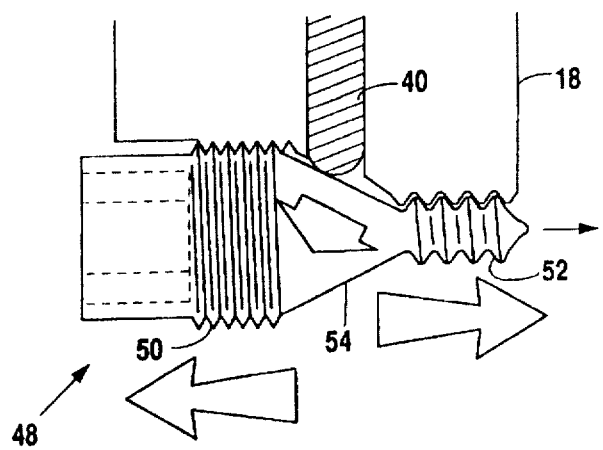
FIG. 10 is an elevational, partial cross sectional view of the interaction between the cam nut, the ring unit and the cam insert of Applicant's rib carriage at the final stage of insertion of the cam nut into the recess of the ring unit.

Referring principally to FIGS. 1, 9 and 10, a special cam nut system is utilized in the preferred embodiment of Applicant's rib carriage 10 to secure the cam insert 40 in place and to all but eliminate any probability that the cam insert 40 will partially or completely dislodge from the ring unit 16 with obvious undesirable consequences. To accomplish this goal, Applicant's invention prescribes a partially cone-shaped cam nut 48 with two separate thread segments 50 and 52. Thread segment 50, the outermost segment, is an SAE thread while the innermost segment, segment 52, is a coarser standard thread. Intervening thread segments 50 and 52 is a smooth, conical segment 54. The exterior face 56 of cam nut 48 exhibits a hexagonal recess 58 for interaction with a hex head screw driver (not shown in the drawings).

Referring principally to FIGS. 1, 6, 9 and 10, cam insert 40 and ring unit 16 respectively exhibit complimentary recesses 60 and 62 for jointly defining a suitable orifice into which cam nut 48 may be received. Recess 62 of ring unit 16 is defined by two separate portions 64 and 66, portion 64 exhibiting fine threading which is complimentary to the SAE threading of thread segment 50, and portion 66 exhibiting coarser threading which is complimentary to the standard threading of thread segment 52. As is clear from inspection of FIGS. 9 and 10, interaction of thread segments 50 and 52 respectively with portions 64 and 66 of recess 62 creates opposing forces due to the differing rate of relative advancement of the two thread segments 50 and 52 with respect to portions 64 and 66 of recess 62. These opposing forces tend to bear on each of the threads involved in the interaction between cam nut 48 and ring unit 16 to thereby greatly enhance the frictional and mechanical resistance to any force which would tend to loosen cam nut 48.

Figure 5:
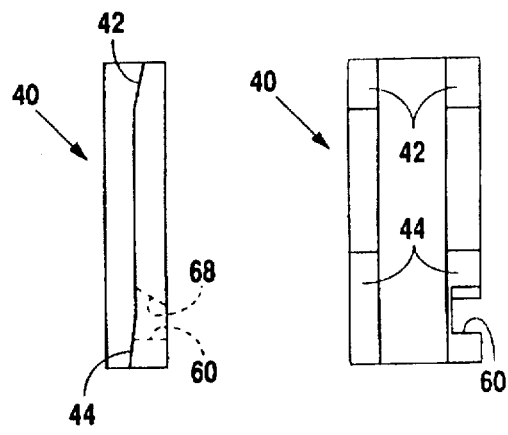
FIG. 5 is an elevational side view of the cam insert of Applicant's rib carriage.
Figure 6:
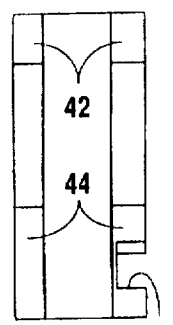
FIG. 6 is an elevational front view of the cam insert of Applicant's rib carriage.

Referring principally to FIGS. 1 and 5, recess 60 of cam insert 40 lacks threading, but is contoured so as to exhibit a cam incline 68 on its upper margin which cam incline 68 interacts with conical segment 54 of cam nut 40 to further urge cam insert 40 into its extreme inserted position with respect to ring unit 16. This interaction adds yet another frictional interaction directed in a third vector for further securing the relative positions of the ring unit 16, the cam insert 40 and the cam nut 48.

Figure 11:
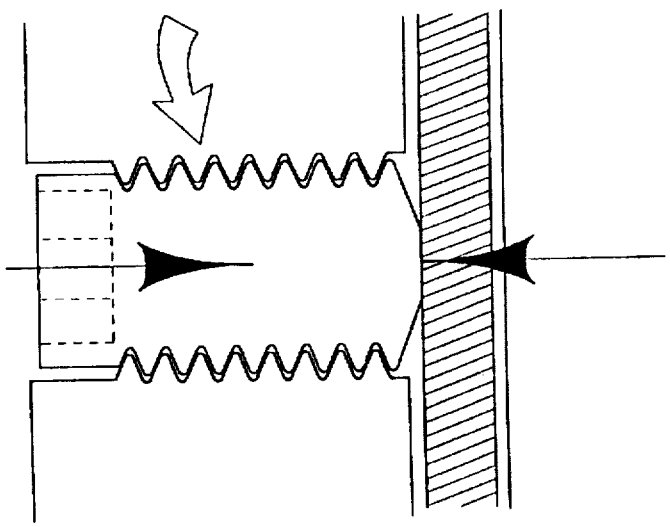
FIG. 11 is an elevational, partial cross sectional view of the thread and rod interaction involved in a conventional allen nut system (shown as means of comparison, not as part of any preferred embodiment of Applicant's invention).

Referring principally to FIG. 11, the cam nut system just described offers significant advantages over a simple allen nut type locking scheme which would exhibit a singular threading system. In such a latter system, only a portion of the threads are actively engaged in maintaining the nut in place and the resulting force vectors are opposed in such a manner as to promote, rather than impede withdrawal of the nut from its threaded recess.

Figure 14:
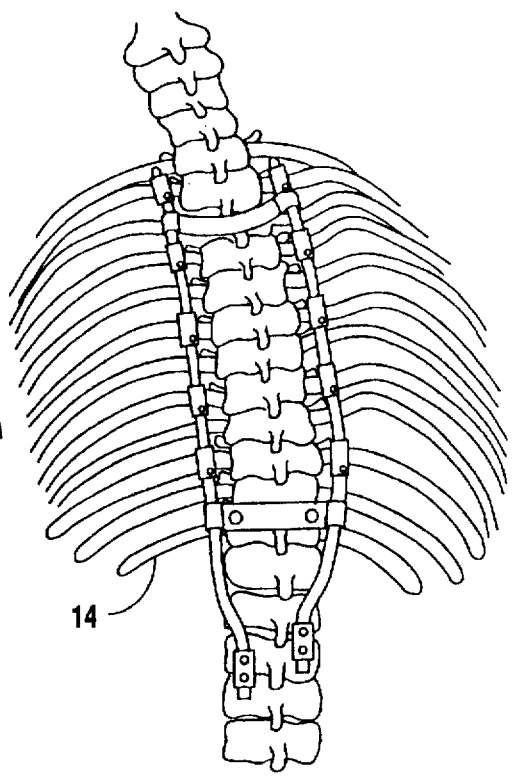
FIG. 14 is a posterior view representation of spinal rods implanted according to Applicant's invention after rotation of the rods to effect correction of the scoliotic curvature.
Figure 13:
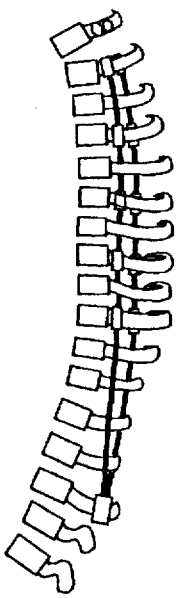
FIG. 13 is a lateral view representation of spinal rods implanted according to Applicant's invention prior to rotation of the rods to effect correction of the scoliotic curvature.
Figure 15:
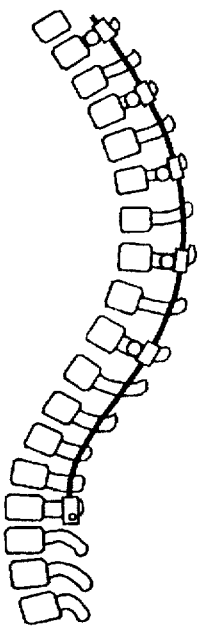
FIG. 15 is a lateral view representation of spinal rods implanted according to Applicant's invention after rotation of the rods to effect correction of the scoliotic curvature.

Referring to FIGS. 16, 17, 18 and 19, spinal rods 12 are integrated into a unitary therapeutic device by way of arched cross link bridge units 70 (shown in use in FIG. 14). Each bridge unit 70 includes a cross link 72 with integral cross link rod clamp hooks 74 at either end (formed to partially envelope the spinal rod 12 which is to be used). The body portion 76 of the cross link 72 is curved accordingly to a fixed and stationary radius of curvature. Two recesses 78 are formed into the anterior surface of the cross link 72 and are sized and shaped for receiving cradle bar 82 therein. The anterior face the cross link 72 within the bounds of recesses 78 is defined by a slightly smaller radius of curvature than that defining the over-all curvature of the cross link 72. The center point of the radius of curvature is shifted slightly so as to gradually deepen the recess 78 near the lateral margin nearest the adjacent clamp hook 74. This configuration permits a fulcrum-like compression of a spinal rod 12 between the clamp hooks 74 of the cross link 72 and the clamp hooks 84 of the cradle bar 82.

Figure 16:
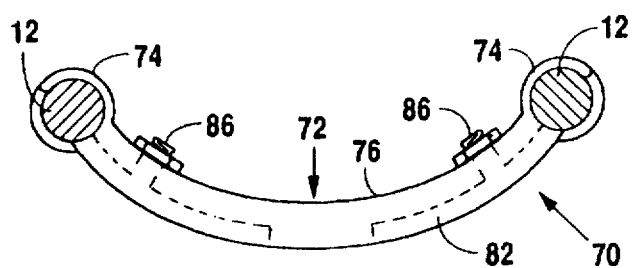
FIG. 16 is a elevational, partially cross sectional side view of the arched cross link bridge component of Applicant's spinal instrumentation system.
Figure 17:
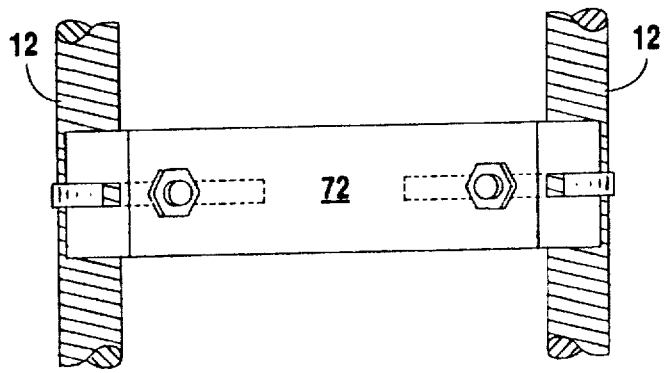
FIG. 17 is a top plan, partially cross sectional top view of FIG. 16.

Referring principally to FIGS. 16 and 17, the cradle bars 82, as mentioned, include clamp hooks 84 which, like clamp hooks 74 of the cross links 78, are sized and shaped to partially encircle a spinal rod 12. Both clamp hooks 74 and clamp hooks 84 should define slightly less than a full 180 radians of curvature within so as to leave a very small gap between their respective termini when grasping a spinal rod 12 as depicted in the drawings. This insures proper grasping of the spinal rods 12 assuming the rest of the bridge unit 70 is properly configured for securely grasping the spinal rods 12 between clamp hooks 74 and 84. The posterior face of each cradle bar 82 exhibits a threaded stud 86 which is to extend through a hole 80 which extends through the cross link 72 within the bounds of each of recesses 78.

Figure 20:
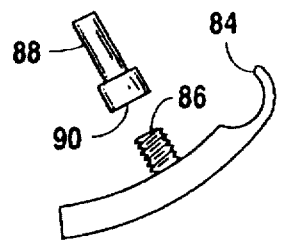
FIG. 20 is a side elevational view of a spinal rod clamp for use with the arched cross link bridge of FIGS. 18 and 19.
Figure 18:
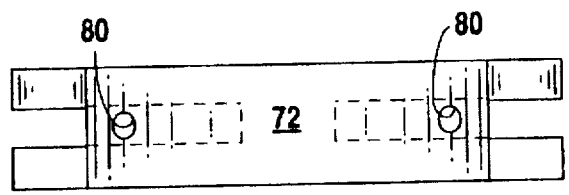
FIG. 18 is a top plan view of the arched cross link bridge of Applicant's spinal instrumentation system, less the spinal rod clamps.
Figure 21:
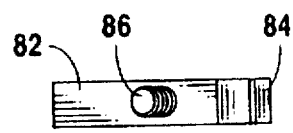
FIG. 21 is a top plan view of the spinal rod clamp of FIG. 20.
Figure 19:
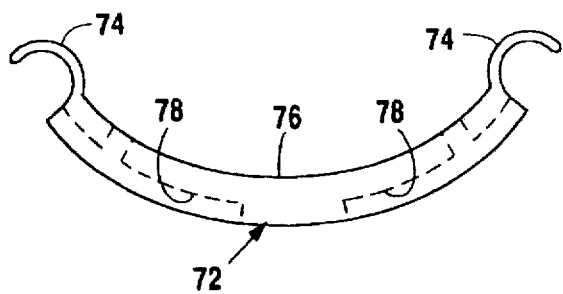
FIG. 19 is a side elevational view of FIG. 18.

Referring principally to FIG. 20, an extender rod 88 is provided for use in installing the bridge unit 70 and exhibits a threaded socket 90 which is sized and threaded to threadingly receive stud 86 therein. The extender rod overall is sized to pass through hole 80 in cross link 72 and is intended to aid in manipulating the cradle bar 82 relative to the cross link 72 to properly position the cradle bar 82 during implantation. Once the cradle bar 82 is in the appropriate position, the extender rod 88 is to be removed and rod compression nuts 81 are threaded onto studs 86 of each of the two cradle bars 82 to securely clutch each spinal rod 12 between each respectively paired clamp hook 84 of the cradle bars 82 and clamp hook 74 of cross link 72.

The methodology associated with implantation and operation of Applicant's instrumentation is generally straight forward. The ribs 14 to which Applicant's instrumentation is to be anchored, are accessed by conventional incision methods. The rib carriages 10 are threaded about the osseous rib following appropriate incisions of the periosteum. Attaching the rib carriages 10 subperiosteally protects the underlying lung (not shown in any drawings).

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A method for manipulating curvature of a human spine comprising the steps of:

selecting a first spinal rod and contouring said first spinal rod to define, in three dimensions, an at least partially corrected first dorsal contour of a first plurality of first ribs substantially along a first line lying in a first plane which first plane lies closely adjacent to said spine on a first side of said spine;

selecting a second spinal rod and contouring said second spinal rod to define, in three dimensions, an at least partially corrected second dorsal contour of a second plurality of second ribs substantially along a second line lying in a second plane which second plane lies closely adjacent to said spine on a second side of said spine;

selecting a third plurality of first rib carriages configured for attachment to said first spinal rod and respectively to each of a like fourth plurality of said first ribs on a first side of said spine of a recipient of said apparatus;

selecting a fifth plurality of second rib carriages configured for attachment to said second spinal rod and respectively to each of a like sixth plurality of said second ribs on a second side of said spine of said recipient of said apparatus;

attaching each of said first rib carriages respectively to each of said first ribs of said fourth plurality of said first ribs along said first line;

attaching each of said second rib carriages respectively to each of said second ribs of said sixth plurality of said second ribs along said second line;

attaching each of said first rib carriages to said first spinal rod; and attaching each of said second rib carriages to said second spinal rod wherein each of said first and said second rib carriages comprises a ring unit and a cam insert, each said ring unit including a loop structure on a first side of said ring unit and defining, on a second side of said ring unit, a spinal rod recess for partially enveloping a portion of one of said spinal rods, each said ring unit further exhibiting cam insert mating means adjacent said spinal rod recess for mechanically mating with said cam insert, said cam insert being sized and configured relative to said cam insert mating means whereby when said cam insert is mated with said cam insert mating means, said cam insert exerts a first force on a first side of said one of said spinal rods and a second force, oppositely directed from said first force, on said ring unit, said first and said second forces being vectored whereby said ring unit exerts a third force on a second side of said one of said spinal rods, substantially opposite said first side of said one of said spinal rods, said third force being applied in a substantially opposing direction from said first force whereby said one of said spinal rods is lodged between and substantially immobilized relative to said rib carriage.

2. The method of claim 1 wherein each of said first and said second rib carriages comprises rib encircling means and spinal rod clamping means, said rib encircling means and said spinal rod clamping means of each said rib carriage being disposed with respect to each other whereby, when each said rib encircling means is attached to respective said first or said second ribs, said spinal rod clamping means are oriented for maintaining a substantially rigid attachment between said rib encircling means and said spinal rod attachment means for maintaining a substantially rigid spatial relation between said spinal rod and said respective said first or said second ribs.

3. The method of claim 2 further comprising the steps of:

selecting a bridge unit, said bridge unit having first spinal rod attachment means on a first end of said bridge unit, and second spinal rod attachment means on a second end of said bridge unit, said first and said second spinal rod attachment means being configured for secure, substantially rigid affixation respectively to said first and second spinal rods;

attaching said first spinal rod attachment means to said first spinal rod; and attaching said second spinal rod attachment means to said second spinal rod.

4. The method of claim 1 further comprising the steps of:

selecting a bridge unit, said bridge unit having first spinal rod attachment means on a first end of said bridge unit, and second spinal rod attachment means on a second end of said bridge unit, said first and said second spinal rod attachment means being configured for secure, substantially rigid affixation respectively to said first and second spinal rods;

attaching said first spinal rod attachment means to said first spinal rod; and attaching said second spinal rod attachment means to said second spinal rod.

5. The method of claim 4 wherein each of said first and said second rib carriages comprises rib encircling means and spinal rod clamping means, said rib encircling means and said spinal rod clamping means of each said rib carriage being disposed with respect to each other whereby, when each said rib encircling means is attached to respective said first or said second ribs, said spinal rod clamping means are oriented for maintaining a substantially rigid attachment between said rib encircling means and said spinal rod attachment means for maintaining a substantially rigid spatial relation between said spinal rod and said respective said first or said second ribs.

6. The method of claim 1 further comprising the steps of:

selecting a bridge unit, said bridge unit having first spinal rod attachment means on a first end of said bridge unit, and second spinal rod attachment means on a second end of said bridge unit, said first and said second spinal rod attachment means being configured for secure, substantially rigid affixation respectively to said first and second spinal rods;

attaching said first spinal rod attachment means to said first spinal rod; and attaching said second spinal rod attachment means to said second spinal rod.

* * * * *